(12) United States Patent
Bean et al.

(10) Patent No.: US 10,568,853 B2
(45) Date of Patent: Feb. 25, 2020

(54) METHODS OF TREATING MUSCLE CRAMPING AND RELATED COMPOSITIONS

(71) Applicant: FLEX PHARMA, INC., Boston, MA (US)

(72) Inventors: Bruce P. Bean, Waban, MA (US); Donald MacKinnon, New York, NY (US); Roderick MacKinnon, New York, NY (US)

(73) Assignee: Cliff-Cartwright Corporation, Wellesley Hills, MA (US)

( * ) Notice: Subject to any disclaimer, the term of this patent is extended or adjusted under 35 U.S.C. 154(b) by 0 days.

(21) Appl. No.: 15/241,986

(22) Filed: Aug. 19, 2016

(65) Prior Publication Data
US 2016/0367506 A1 Dec. 22, 2016

Related U.S. Application Data

(60) Division of application No. 14/450,384, filed on Aug. 4, 2014, now Pat. No. 9,937,135, which is a continuation of application No. 13/191,941, filed on Jul. 27, 2011, now abandoned.

(60) Provisional application No. 61/368,059, filed on Jul. 27, 2010.

(51) Int. Cl.
| | | |
|---|---|---|
| *A61K 31/137* | (2006.01) | |
| *A23L 9/10* | (2016.01) | |
| *A61K 31/165* | (2006.01) | |
| *A61K 9/00* | (2006.01) | |
| *A61K 9/06* | (2006.01) | |
| *A61K 9/08* | (2006.01) | |
| *A61K 31/12* | (2006.01) | |
| *A61K 31/16* | (2006.01) | |
| *A61K 31/19* | (2006.01) | |
| *A61K 31/194* | (2006.01) | |
| *A61K 31/375* | (2006.01) | |
| *A61K 33/42* | (2006.01) | |
| *A61K 36/906* | (2006.01) | |
| *A23L 2/52* | (2006.01) | |
| *A61K 36/54* | (2006.01) | |
| *A61K 36/81* | (2006.01) | |
| *A61K 36/9068* | (2006.01) | |

(52) U.S. Cl.
CPC ............. *A61K 31/165* (2013.01); *A23L 2/52* (2013.01); *A61K 9/0053* (2013.01); *A61K 9/0095* (2013.01); *A61K 9/06* (2013.01); *A61K 9/08* (2013.01); *A61K 31/12* (2013.01); *A61K 31/16* (2013.01); *A61K 31/19* (2013.01); *A61K 31/194* (2013.01); *A61K 31/375* (2013.01); *A61K 33/42* (2013.01); *A61K 36/54* (2013.01); *A61K 36/81* (2013.01); *A61K 36/906* (2013.01); *A61K 36/9068* (2013.01); *A23V 2002/00* (2013.01)

(58) Field of Classification Search
CPC ................................ A23L 9/10; A61K 31/137
See application file for complete search history.

(56) References Cited

U.S. PATENT DOCUMENTS

| | | | |
|---|---|---|---|
| 6,274,177 B1 * | 8/2001 | Wu .................... | A61K 36/9068 424/756 |
| 6,534,086 B1 | 3/2003 | Krumhar | |
| 9,937,135 B2 | 4/2018 | Bean et al. | |
| 2003/0180226 A1 | 9/2003 | Haughton | |
| 2007/0020301 A1 | 1/2007 | Shimagami et al. | |
| 2009/0029345 A1 | 1/2009 | Russell et al. | |
| 2009/0215107 A1 | 8/2009 | Hwang et al. | |
| 2010/0099772 A1 | 4/2010 | Bean et al. | |
| 2012/0027693 A1 | 2/2012 | Bean et al. | |
| 2014/0343156 A1 | 11/2014 | Bean et al. | |

FOREIGN PATENT DOCUMENTS

| | | |
|---|---|---|
| CN | 101040720 A | 9/2007 |
| WO | WO-2009/137686 A1 | 11/2009 |
| WO | WO-2012/015882 A1 | 2/2012 |

OTHER PUBLICATIONS

Bonnie K. McMillen, R.N, B.S.N. ("Home Remedy for Cough." College Health Nurse, University of Pittsburgh at Bradford, Bradford, PA. https://web.archive.org/web/20100301115138/http://www.pitt.edu/~cjm6/sp99cough.html: pp. 1-2. Mar. 1, 2010).*
The George Mateljan Foundation (The World's Healthiest Foods: Visitors Questions. http://www.whfoods.com/genpage.php?tname=answeredquestion&dbid=130: pp. 1-3. Accessed Dec. 10, 2015).*
J. Crow Company ("Cayenne Pepper." J. Crow Company, New Ipswich, NH. http://web.archive.org/web/20080202032007/http://www.jcrows.com/cayenne.html#prostate: p. 28. Feb. 2, 2008).*
Definition of Gel by Merriam-Webster. https://www.merriam-webster.com/dictionary/gel. Accessed Jan. 4, 2018. (Year: 2018).*
"Rote Liste 2004" Jan. 1, 2004, Frankfurt/Main pp. 62 090-66 092.
Anonymous "Characterizing Soy Sauce" Retrieved from the Internet: URL: http://www.kikkomanusa.com/foodmanufacturers/soysaucebasics/characterizingsoysauce.php [retrieved on Jun. 6, 2014].
CureZone, Internet message board, http://www.curezone.org/forums/fm.asp?i=1519224#i, Ginger, cinnamon, turmeric, cayenne pepper and spirits posted Nov. 5, 2009.
JIN + JA website: http://www.drinkjinja.com/pages/about-us, Mar. 31, 2013 (date as provided by the Internet Archive Wayback Machine, <http://archive.org/web>).

(Continued)

*Primary Examiner* — Rachael E Bredefeld
*Assistant Examiner* — Chris E Simmons
(74) *Attorney, Agent, or Firm* — Goodwin Procter LLP

(57) ABSTRACT

Described herein are compositions comprising capsaicin and methods of treating muscle cramping in a subject, comprising orally administering to the subject a composition comprising capsaicin and an excipient.

13 Claims, 8 Drawing Sheets

(56) References Cited

OTHER PUBLICATIONS

Ofner, Reconstitutable Oral Suspensions, Chapter 6, pp. 243-258, in Pharmaceutical Dosage Forms. vol. 2: Disperse Systems, New York Marcel Dekker, Inc., 1996.

Opinion of the Scientific Committee on Food on Capsaicin (European Commission, Health & Consumer Protection Directorate-General, Feb. 28, 2002.

Supplementary European Search Report for European Application No. EP 11813088.9 dated Jun. 6, 2014.

Vriens et al., "Herbal compounds and toxins modulating TRP channels," Curr Neuropharmacol. 6:79-96 (2008).

Written Opinion for International Application No. PCT/US11/45480, dated Dec. 14, 2011 (7 pages).

Montell, "New light on TRP and TRPL," Mol Pharmacol. 52:755-763 (1997).

International Search Report for International Application No. PCT/US2011/045480 dated Dec. 14, 2011 (3 pages).

\* cited by examiner

Figure 1
A : 1/800,000 Capsicum extract
B : 1/5,000 Cinnamon extract
C : 1/12,000 Ginger extract
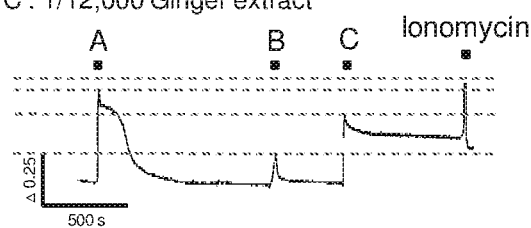
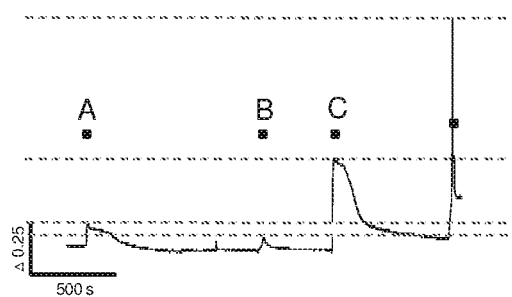
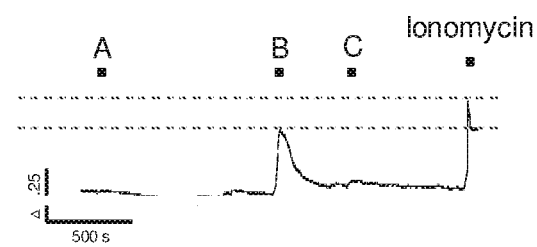
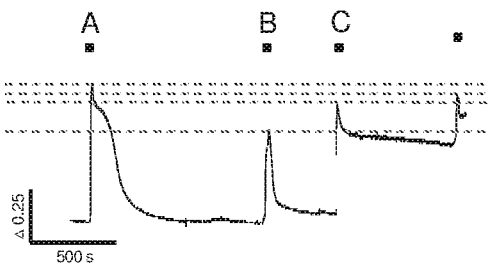
A : 1/20,000,000 Capsicum extract
C : 1/2,000,000 Ginger extract
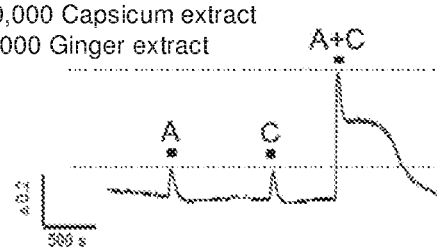
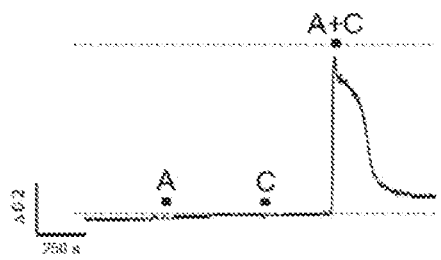

US 10,568,853 B2

METHODS OF TREATING MUSCLE CRAMPING AND RELATED COMPOSITIONS

CROSS-REFERENCE TO RELATED APPLICATIONS

This application is a division of U.S. application Ser. No. 14/450,384, filed Aug. 4, 2014, which is a continuation of U.S. application Ser. No. 13/191,941, filed Jul. 27, 2011, now abandoned, which claims the benefit of U.S. Provisional Application No. 61/368,059, filed Jul. 27, 2010. The contents of each of the foregoing applications are hereby incorporated by reference in their entirety.

BACKGROUND OF THE INVENTION

In general, the invention relates to methods and compositions for preventing, treating or ameliorating muscle cramping and/or accelerating nerve-muscle recovery from exercise fatigue.

Muscle cramps, the involuntary and forceful contraction of muscles, are often painful and can last for a prolonged period of time. Muscle contractions and cramping can be triggered by exercise and can also occur spontaneously (e.g., nocturnal or night cramps). The underlying physiological mechanism of muscle cramping is unknown. Recent understanding has led to the hypothesis that cramping results from excessive electrical firing of the neurons (motor neurons) that project from the spinal cord and trigger contraction of skeletal muscles (Schwellnus, *Br J Sports Med.* 43:401-8, 2009; Miller et al, *Med Sci Sports Exerc.* 42:953-61, 2010). Recovery from strenuous exercise can be associated with neuromuscular irritability, associated with neuromuscular fatigue, that may or may not be associated with the development of frank cramps. Few treatments and therapeutic regimens are available to alleviate this neuromuscular irritability.

There exists a need in the art for improved methods and compositions for preventing, treating, and ameliorating muscle cramping and/or accelerating nerve-muscle recovery from exercise fatigue by reducing neuromuscular irritability. As shown herein, compositions that include activators of TRP and ASIC channels may be useful to prevent, treat, or ameliorate muscle cramping and/or accelerate nerve-muscle from, e.g., exercise fatigue. Further, these compositions can be useful in treating neuromuscular irritability that may or may not be associated with the development of frank cramps.

SUMMARY OF THE INVENTION

The present invention is directed to the prevention, treatment or amelioration of muscle cramps and/or accelerating nerve-muscle recovery from exercise fatigue using a composition with an activator of TRPV1 channels, an activator of TRPA1 channels, and/or an activator of ASIC channels.

a first aspect, the invention features a method for treating muscle cramps in a subject in need thereof (e.g., a human), the method including the step of administering to the subject a composition that includes an effective amount of one or more TRPV1 channel activators, TRPA1 channel activators, or ASIC channel activators, or any combination thereof.

The invention also features a method for treating musculoskeletal irritability in a subject in need thereof. The method includes administering to the subject a composition that includes an effective amount of one or more TRPV1 channel activators, TRPA1 channel activators, or ASIC channel activators, or any combination thereof.

In still another aspect, the invention features a method for improving muscle recovery (e.g., muscle recovery following exercise) in a subject in need thereof, where the method includes administering to the subject a composition that includes an effective amount of one or more TRPV1 channel activators, TRPA1 channel activators, or ASIC channel activators, or any combination thereof.

In any of the foregoing methods, the composition can be, e.g., an oral formulation (e.g., a liquid, beverage, gel, semi-solid, frozen liquid, lozenge, hard candy, dissolving strip, or spray).

In certain embodiments of any of the methods described herein, the composition is administered to the subject prior to exercise, during exercise, or following exercise (e.g., within 0-120 minutes prior to exercise, or within 0-360 minutes, 0-15 minutes, or 2-6 hours following exercise.

Muscle cramps that can be treated or prevented using the methods and compositions described herein include, e.g., muscle cramps resulting from exercise, nocturnal cramps, and menstrual cramps.

In particular embodiments of any of the methods described herein, the composition includes an effective amount of two or three different TRP channel activators independently selected from:
   (a) capsaicin or other capsaicinoids;
   (b) cinnamaldehyde or cinnamon oil; and
   (c) gingerols.

In other embodiments of any of the methods described herein, each channel activator, independently, includes between 0.001% to 1% weight percent of a composition that is a solid, semi-solid, gel, or chewing gum, or 0.001 to 1% (v/v) of a composition that is a liquid, beverage, or spray.

In still other embodiments of any of the methods described herein, the composition is any of the compositions described herein.

The invention also features a composition formulated for oral ingestion by a subject. The composition includes an effective amount of one or more channel activators (e.g., one or more substantially pure channel activators) selected from TRPV1 channel activators, TRPA1 channel activators, and ASIC channel activators. Desirably, the composition is a liquid, beverage, gel, semi-solid, frozen liquid, lozenge, hard candy, dissolving strip, or spray.

Desirably, the channel activator is capable of activation of a channel in a gastroesophogeal neuron when administered to a subject The channel activators can be substantially pure or not substantially pure (e.g., part of a crude extract).

In certain embodiments, the channel activators are capable of activation of a channel in a gastroesophogeal neuron when administered to a subject.

The TRPV1 channel activator can be is a capsaicinoid (e.g., capsaicin). In one example embodiments, the composition contains capsaicin but is substantially free of dihydrocapsaicin.

The TRPV1 channel activator can also be, e.g., oleoylethanolamide, N-oleoyldopamine, 3-methyl-N-oleoyldopamine, oleamide, capsiate, a 1-monoacylglycerol having C18 and C20 unsaturated and C8-C12 saturated fatty acid, a 2-monoacylglycerol having C18 and C20 unsaturated fatty acids, miogadial, miogatrial, polygodial, a terpenoid with an alpha,beta-unsaturated 1,4-dialdehyde moiety, sanshool, evodiamine, acesulfame-K, cyclamate, $CuSO_4$, $ZnSO_4$, $FeSO_4$, arvanil, anandamide, N-arachidonoyl-dopamine, flufenamic acid dopamide, a dopamine amide of fenamic acid, 4-hydroxynonenal, or 1-[2-(1-adamantyl)ethyl]-1-pentyl-3-[3-(4-pyridyl)propyl]urea, or gingerol.

Suitable TRPA1 channel activators include, e.g., allyl isothiocyanate, gingerols, cinnamaldehyde, acrolein, farnesyl thiosalicylic acid, $\Delta_9$-tetrahydrocannabinol, eugenol, shogaols, nicotine, nicotine derivatives or analogs, methyl salicylate, cinnamaldehyde, allicin, diallyl sulfide, diallyl disulfide, diallyl trisulfide, sanshools, and farnesyl thioacetic acid.

Each channel activator can be present, e.g., between 0.001% to 1% (w/w) or 0.001 to 1% (v/v) of a composition.

In certain embodiments, the composition includes no more than one TRPV1 channel activator, TRPA1 channel activator, or ASIC channel activator. In still other embodiments, the composition includes a TRPV1 channel activator and a TRPA1 channel activator (e.g., a substantially pure TRPA1 channel activator and/or a substantially pure TRPV1 channel activator). In yet other embodiments, the composition includes no more than one TRPV1 channel activator and no more than one TRPA1 channel activator. And in still other embodiments, the composition includes a second TRPV1 channel activator and/or a second TRPA1 channel activator.

The composition includes can include an effective amount of an ASIC channel activator (e.g., a substantially pure AMC channel activator). In some embodiments, the ASIC channel activator (e.g., a substantially pure ASIC channel activator) is capable of activation of an ASIC channel in a gastroesophogeal neuron when administered to a subject.

In certain embodiments, the ASIC channel activator is an acidulant that is acetic acid. In further embodiments, the composition is a liquid or beverage that has an acetic acid concentration ranging from 0 M to 0.1 M (e.g., from 0 M to 0.001 M). In other embodiments, the ASIC channel activator is an acidulant selected from phosphoric acid, citric acid, malic acid, succinic acid, tartaric acid, fumaric acid, and ascorbic acid.

The invention also features a composition that includes an effective amount of two or three different TRP channel activators independently selected from capsaicin or another capsaicinoid; cinnamaldehyde or cinnamon oil; and gingerols, where the composition is an oral formulation that is a liquid, beverage, gel, solid, semi-solid, chewing gum, or spray.

In certain embodiments, the composition includes an effective amount of two or three different TRP channel activators independently selected from: capsicum; cinnamon volatile oil; and ginger oleoresin. For example, the composition can include each of the components.

In some embodiments the capsaicinoid is present in 0.001% to 1% (w/w) or 0.001% to 1% (v/v); and/or the cinnamaldehyde or cinnamon oil is present in 0.001% to 10% (w/w) or 0.001% to 10% (v/v); and/or the gingerols are present in 0.001% to 10% (w/w) or 0.001% to 10% (v/v).

In one example, the composition is a beverage that optionally includes a sweetener.

A composition of the invention can also include an acidulant selected from acetic acid, phosphoric acid, citric acid, malic acid, succinic acid, tartaric acid, fumaric acid, acetic acid, and ascorbic acid.

The composition can also include a potassium salt at a concentration of between about 0.02% and about 7% by weight based on total volume of the liquid, beverage, or gel.

The composition can be a liquid, beverage, or gel that also includes a viscosity modifier, such as collagen, gellan gum, carbohydrate gel-forming polymers, carob bean gum, locust bean gum, carrageenan, alginic acid, sodium alginate, potassium alginate, ammonium alginate, calcium alginate, agar, guar gum, xanthan gum, carboxymethyl cellulose, clear starch, pectin, gelatin, arrowroot, cornstarch, katakuri starch, potato starch, sago, tapioca, furcellaran, or sodium pyrophosphate. In certain embodiments, the composition has a viscosity between about 1000 and about 10000 cP (e.g., 1000, 2000, 3000, 4000, 5000, 6000, 7000, 8000, 9000, or 10000 cP).

In some embodiments of any compositions described herein, the composition also includes one or more of electrolytes, sweeteners, flavoring agents, vitamins, minerals, amino acids, or preservatives.

In certain embodiments of any compositions described herein, the composition is a beverage or gel that is made by reconstituting a dry powder with an aqueous fluid (e.g., water).

In other embodiments of any compositions described herein, the composition is a packaged beverage. In some embodiments, the packaged beverage is provided in a unit that contains between 10-1000 mL (e.g., between 10-500 mL) of the beverage.

In still other embodiments of any compositions described herein, the composition is a gel. In certain embodiments, the composition is a packaged gel. In further embodiments, the packaged gel is provided in a unit that contains between 5-100 grams (e.g., between 30-40 grams) of the gel.

In some embodiments of any of the methods described herein, the composition of (1) or (2) has a pH that is greater than about 2.5 (e.g., the pH of the composition is greater than about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, or 6.5). For example, the composition of (1) or (2) can have a pH of about 4 to about 9, about 5 to about 9, or 6.5 to about 7.5.

In certain embodiments, the composition is a liquid or beverage that does not include acetic acid or a salt thereof, or that has an acetic acid concentration ranging from 0 M to 0.1 M, 0 M to 0.001 M, is substantially 0 M.

In some embodiments of any of the compositions described herein, the TRPV1 channel activator is a proton concentration of $10^{-7}$ M to $10^{-2}$ M (pH 2-pH 7), e.g. produced by inclusion of acidulants such as acetic acid, phosphoric acid, citric acid, malic acid, succinic acid, tartaric acid, fumaric acid, and ascorbic acid.

In some embodiments of any of the methods or compositions described herein, where the composition includes vinegar (e.g., apple cider vinegar), the composition includes no more than one of garlic (e.g., garlic extracts) or ginger (e.g., ginger extracts).

In other embodiments of any of the methods or compositions described herein, where the composition includes garlic (e.g., garlic extracts), the composition includes no more than one of vinegar (e.g., apple cider vinegar) or ginger (e.g., ginger extracts).

In some embodiments of any of the methods or compositions described herein, where the composition includes ginger (e.g., ginger extracts), the composition includes no more than one of garlic (e.g., garlic extracts) or vinegar (e.g., apple cider vinegar).

Any of the compositions described herein can be used in any of the methods described herein (e.g., to treat muscle cramps such as nocturnal cramps or menstrual cramps, or muscle cramps resulting from exercise, to treat musculoskeletal irritability, or to improve muscle recovery). The compositions used in the methods can include substantially pure channel activators. In other embodiments of any of the compositions or methods described herein, the TRP channel (e.g., a TRPV1 or TRPA1 activator) activator and/or the ARC channel activator is not substantially pure. For example, a composition can include a mixture of capsaicinoids (e.g., as capsicum or between 0.0001-0.01 mgs/mL of total capsaicinoids). In some embodiments, the channel activators are provided as extracts suitable for human consumption.

In still another aspect, the invention features a method of preparing any of the compositions described herein for treating or ameliorating muscle cramps in a subject in need thereof, or for treating musculoskeletal irritability in a subject in need thereof, the method including the use of TRP or ASIC channel activator compounds that are substantially pure with an excipient to provide a composition that is a liquid, beverage, gel, solid, semi-solid, chewing gum, or spray.

By "ASIC channel" is meant an acid sensing ion channel that is opened by low pH and can excite certain neurons or muscle fibers or other cells.

By "acidulant" is meant an acidic compound (e.g., citric acid) used to lower the pH of a composition, e.g., the pH can be lowered in the range of 2.5-6.5 (e.g., pH of 2.5, 3.0, 3.5, 4.0, 4.5, 5.0, 5.5, 6.0, or 6.5).

By "activator," "compound that activates," or "agonist" is meant a molecule that stimulates a biological response.

By "administering" and "administration" is meant a mode of delivery. A daily dosage can be divided into one, two, three or more doses in a suitable form to be administered one, two, three or more times throughout a time period. In preferred embodiments of the present invention, compositions and solutions are administered orally.

By "beverage" is meant a composition that is not in solid or gas form, such as a liquid or semi-liquid that is designed to enter into the mouth of a subject and be orally consumed or ingested. A beverage may be in a ready-to-drink liquid form (e.g., may be consumed without modification) or in a liquid, solid, or concentrated form, which can be transformed into a ready-to-drink liquid form with an addition of another liquid (e.g., water). See, e.g., *Sports Drinks: Basic Science and Practical Aspects*, Ed. Ronald J. Maughan, CRC Press, 2000.

Where the term "composition" is used to describe a formulation that includes an activator of TRPV1 channels, and/or an activator of TRPA1 channels, and/or an activator of ASIC channels, the term refers to a comestible formulation that is suitable for oral ingestion by the subject (e.g., the human subject). Exemplary compositions that include an activator of TRPV1, TRPA1, and ASIC channels include sprays (e.g., aerosols), powders, chewing gum, ingestible solids, gels, aqueous beverages, dry powder (e.g., a powder that can be directly consumed or that can be reconstituted with liquid to provide a beverage as defined herein), nutritional bars, lozenges, tablets, capsules, wafers, pastes, and the like. Other compositions are described herein.

The term an "effective amount" of a compound as used herein, is that amount sufficient to effect beneficial or desired results, such as the effective treatment of muscle cramps or musculoskeletal irritability or the improvement of muscle recovery following exercise, and, as such, an "effective amount" depends upon the context in which it is being applied. For example, in the context of administering an agent that activates a TRP channel (e.g., TRPV1 or TRPA1) or an ASIC channel, an effective amount of an agent is, for example, an amount sufficient to achieve an increase in TRPV1, TRPA1, or ASIC activity as compared to the response obtained without administration of the agent. The effective amount of active compound(s) used to practice the present invention can also be varied based on, for example, the age, and body weight, of the subject or the nature of the exercise.

The compositions can also include one more excipients that are not activators of TRPV1, TRPA1, and ASIC channels and that are non-toxic and non-inflammatory in a subject (e.g., in a human subject). In some embodiments, the excipient(s) can provide desirable or improved physical and/or chemical properties such as stability, flow, viscosity, rate of disintegration, taste, delivery, etc. Exemplary, non-limiting excipients that can be selected from: a disintegrant (e.g., carmellose, starch, crystalline cellulose, low-substituted hydroxypropyl cellulose, and the like), a binder (e.g., gum acacia, carmellose, gelatin, crystalline cellulose, simple syrup, honey, hydroxypropyl cellulose, povidone, methylcellulose, and the like), a surfactant (e.g., polyoxyl 40 stearate, polysorbate 80, polyoxyethylene hydrogenated castor oil, and the like), an emulsifier (e.g., polyoxyl 40 stearate, sorbitan sesquioleate, polysorbate 80, sodium lauryl sulfate, lauromacrogol, gum arabic, cholesterol, stearic acid, povidone, glyceryl monostearate, and the like), a plasticizer (e.g., glycerin, propylene glycol, macrogol, and the like), a lubricant (e.g., magnesium silicate, carmellose, light anhydrous silicic acid, stearic acid, calcium stearate, magnesium stearate, talc, and the like), a sweetener (e.g., white soft sugar, honey, simple syrup, glucose, saccharin sodium, acesulfame potassium, disodium glycyrrhizinate, and the like), a pH-adjusting agent (e.g., hydrochloric acid, citric acid, sodium hydrogen carbonate, potassium hydroxide, sodium hydroxide, sodium carbonate, and the like), a preservative (e.g., benzoic acid, benzalkonium chloride, ethyl parahydroxybenzoate, butyl parahydroxybenzoate, propyl parahydroxybenzoate, methyl parahydroxybenzoate, and the like), a flavor (e.g., fennel oil, orange oil, cinnamon oil, thymol, orange peel tincture, di-menthol, 1-menthol, eucalyptus oil, and the like), or a coloring agent (e.g., Food Red No. 2, No. 3, No. 40, No. 102, No. 104, No. 105 or No. 106, Food Yellow No. 4 or No. 5, Food Green No. 3, Food Blue No. 1 or No. 2, titanium dioxide, sodium copper chlorophyllin, turmeric, gardenia, annatto dye, kaoliang dye, and the like), or an antioxidant (e.g., ascorbic acid, sodium thiosulfate, tocopherol, sodium hydrogen sulfite, and the like), or any combination thereof.

By "ingestible solid" is meant a solid formulation that can be ingested by a subject (e.g., a human) without toxic effects.

By "muscle cramp" is meant a spontaneous contraction of one or more muscles. A muscle cramp may be associated with strenuous exercise or fatigue or may occur during rest (e.g., a nocturnal cramp). Menstrual cramps are also muscle cramps By "nerve-muscle recovery" or "muscle recovery" is meant the recovery from spontaneous muscle contractions and fatigue following exercise that may or may not be associated with the development of frank cramps.

By "neuromuscular irritability" is meant spontaneous muscle contractions (e.g. associated with muscle fatigue) which may or may not be associated with frank cramps.

By "preventing" or "reducing the likelihood of" is meant reducing the severity, the frequency, and/or the duration of a condition or disorder (e.g., muscle cramping) or the symptoms thereof. For example, reducing the likelihood of or preventing muscle cramping is synonymous with prophylaxis of muscle cramping.

By "subject" is meant a mammal, including, but not limited to, a human or human mammal, such as a bovine, equine, canine, ovine, or feline.

As used herein, and when used in reference to TRPA1, TRPV1, and/or ASIC channel activators, the term "substantially pure" refers to a composition that includes a channel activator in which the composition is free of organic and/or inorganic species that do not activate the TRPA1, TRPV1, and/or ASIC channels, and where 60%, 65%, 70%, 75%, 80%, 85%, 90%, 95%, 97%, 98%, 99%, or 99.5% (w/w) of the composition is a particular channel activator compound. Substantially pure compositions can be prepared and analyzed using standard methods known in the art (e.g., chromatographic separation, extractions, and the like). Substantially pure compositions can include isomeric impurities (e.g., geometric isomers) and/or salts or solvates of a channel activator.

By "treating" or "ameliorating" is meant administering a composition for therapeutic purposes or administering treatment to a subject already suffering from a disorder to improve the subject's condition. By "treating a condition or disorder" or "ameliorating a condition or disorder" is meant that the condition or disorder (e.g., muscle cramping) and the symptoms associated with the condition or disorder are, e.g., alleviated, reduced, cured, or placed in a state of remission. As compared with an equivalent untreated control, such amelioration or degree of treatment is at least 5%, 10%, 20%, 30%, 40%, 50%, 60%, 70%, 80%, 90%, 95%, 99%, or 100%, as measured by any standard technique.

By "transient receptor potential cation channel, subfamily V, member 1" or "TRPV1" is meant a nonselective cation channel that may be activated by physical and/or chemical stimuli. TRPV1 channel activators include, e.g., capsaicinoids and capsaicinoid analogs or derivatives and certain endocannabinoids.

By "transient receptor potential cation channel, subfamily A, member 1" or "TRPA1" is meant a cation channel that is a member of the transient receptor potential channel family. TRPA1 channel activators include, e.g., allyl isothiocyanate, cinnamaldehyde, farnesyl thiosalicylic acid, nicotine and its structural analogues, formalin, hydrogen peroxide, 4-hydroxynonenal, and acrolein.

By "viscosity" is meant a measurement of a fluid's internal resistance to flow (e.g., "thickness"). Viscosity is generally expressed in centipoise (cP) or pascal-seconds.

Other features and advantages of the invention will be apparent from the detailed description and from the claims.

BRIEF DESCRIPTION OF THE DRAWINGS

FIG. 1 shows graphs from 6 sensory neurons isolated from the trigeminal ganglia of rats that illustrate their activation by the capsicum, cinnamon, and ginger extracts that were used in the human experiments. These data show that each agent is capable of acting alone to activate some neurons but also that a combination of agents can produce stronger activation of a larger fraction of neurons. Further, the bottom two records suggest that there can be strongly synergistic activation of neurons by the capsicum extract and the ginger extract when applied in combination.

DETAILED DESCRIPTION

Figure 2:
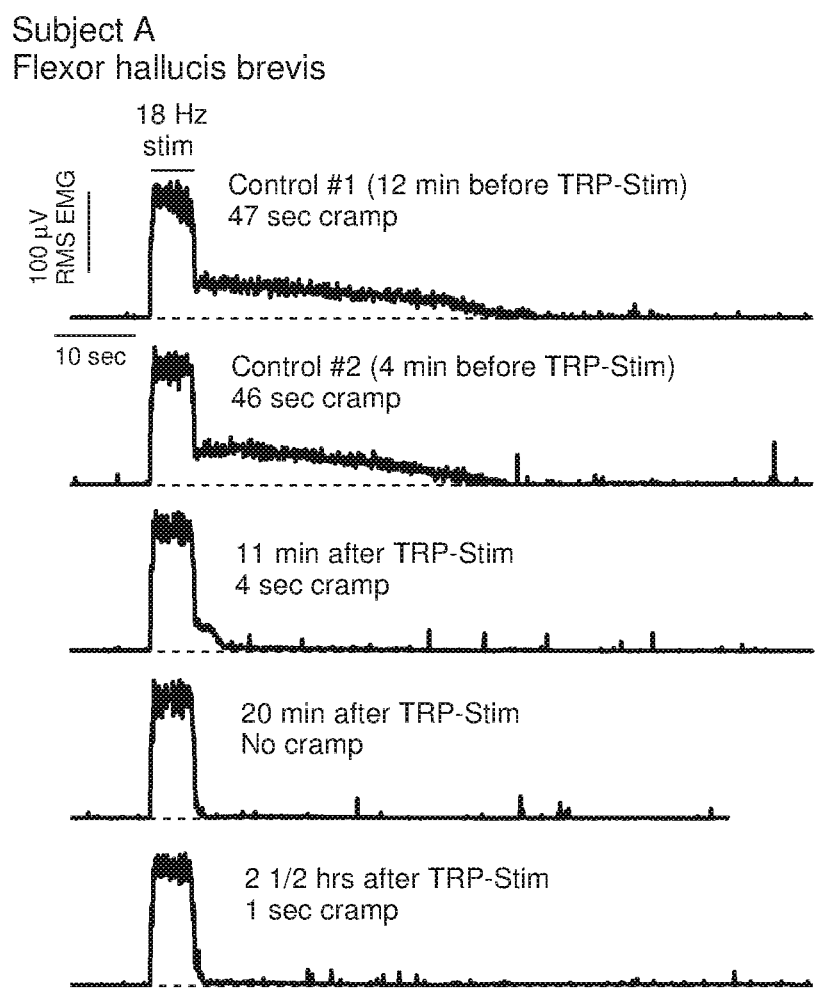
FIG. 2 shows the effect of the TRP-Stim beverage on cramping of the flexor hallucis brevis (FHB) of Subject A. Under control conditions, cramping was reliably induced by stimulating the muscle using an electrical muscle stimulator. After ingestion of 50 mL of a TRP-Stim beverage containing capsaicin and capsaicinoids (TRPV1 agonists), cinnamaldehyde (TRPA1 agonist), and gingerols (TRPA1 and TRPV1 agonists), cramping was very brief after 11 minutes and essentially absent at tests at 20 minutes and 2½ hours after ingestion.

The methods and compositions of the present invention are directed to the treatment or amelioration of muscle cramps using a composition that includes one or more TRPV1 channel activators and/or TRPA1 channel activators and/or ASIC channel activators.

Muscle Cramping

Few treatments and therapeutic regimens are available to alleviate muscle cramping and associated symptoms. Recent work suggests that ingestion of pickle juice can alleviate cramping (Miller et al., *Med. Sci. Sports. Exerc.* 42:953-61, 2010). The mechanism for the efficacy of pickle juice is unknown, although it has been recently proposed (Miller et al., *Med Sci Sports Exerc.* 42:953-61, 2010) that it involves an oropharangeal reflex induced by the sour taste of acetic acid stimulating taste receptors (Kajii et al. *Physiol Behav.* 77:321-5, 2002). Without being bound by theory, we instead hypothesize that pickle juice's efficacy results from the activation of a specific class of non-taste primary sensory neurons that contain nerve endings in the mouth, esophagus, and stomach. These neurons, polymodal C-fiber and A-delta neurons, are distinct from taste neurons, are activated by diverse (polymodal) stimuli, including noxious mechanical, chemical, and thermal stimuli, and are known to contain specific ion channel receptors called Transient Receptor Potential (TRP) ion channels and acid sensing (ASIC) ion channels (Beilefeldt et al., *Am J Physiol Gastrointest Liver Physiol* 294: G130-G138, 2008; Yu et al., *Am J Physiol Gastrointest Liver Physiol* 297: G34-G42, 2009).

We hypothesize that cramps result from excessive firing of motor neurons in the spinal cord, in accordance with recent understanding (Schwellnus, *Br J Sports Med.* 43:401-8, 2009). We further hypothesize that stimulating TRPV1 or TRPA1 or ASIC channels in the nerve endings of primary sensory neurons present in the mouth, esophagus and/or stomach, which project to the spinal cord and brain stem, influence neuromuscular activity by altering activity of neural circuits in the spinal cord or brainstem. TRPV1, TRPA1, and ASIC channels are known to be present in gastroesophageal polymodal sensory neurons that mediate transmission of a variety of noxious stimuli, including mechanical, chemical, and thermal stimul (Beilefeldt et al., *Am J Physiol Gastrointest Liver Physiol* 294: G130-G138, 2008; Yu et al., *Am J Physiol Gastrointest Liver Physiol* 297: G34-G42, 2009). These primary sensory neurons project to the spinal cord and brain stem, where they release glutamate and a variety of neuropeptides (e.g., calcitonin gene-related peptide (CGRP) and substance P). These transmitters act broadly on other types of neurons within the spinal cord and brain stem circuitry, including neurons that release GABA, glycine, and serotonin in the spinal cord, which can in turn inhibit firing of motor neurons. Activity of inhibitory neurons in the spinal cord and brain stem may thus be triggered by stimulation of molecular targets (e.g., TRPV1 and TRPA1 and ASIC channels) present in primary sensory nerve endings in the mouth, esophagus and/or stomach, resulting in inhibition of the motor neurons whose excessive firing is responsible for muscle cramping. In support of this hypothesis, some cramps can be prevented by local nerve block and appear to result from impairment of function of GABAergic interneurons in the spinal cord (Obi et al., *Muscle and Nerve* 6:1228-1231, 1993).

We also hypothesize that spontaneous muscle contractions during recovery from exercise fatigue also arise from excessive firing of motor neurons in the spinal cord and can similarly be reduced by stimulating TRPV1, TRPA1, and/or ASIC channels in the nerve endings of primary sensory neurons present in the mouth, esophagus and/or stomach, which project to the spinal cord and brain stem. By reducing spontaneous muscle contractions stimulation of TRPV1, TRPA1, and/or ASIC channels in nerve endings within the esophagus and/or stomach can accelerate neuromuscular recovery following exercise fatigue.

Compositions

The compositions described herein are comestible formulations suitable for oral consumption by a subject (e.g., by a human) and include one or more activators of TRPV1, TRPA1, and/or ASIC channels as well as one or more optional excipients as described herein. Exemplary, non-limiting compositions include those that are solids (e.g., chews or chewing gums), liquids (e.g., beverages), and gels.

TRPV1 Channel Activators

Compounds that activate TRPV1 that may be used in the compositions of the present invention include, for example, capsaicin, capsaicin analogs and derivatives (e.g., capsaicinoids), and any other compound that activates TRPV1, examples of which are described herein. Modulators of TRPV1 activity are known in the art (see, e.g., Harteneck et al., "Synthetic modulators of TRP channel activity," *Adv Exp Med Biol.* 704:87-106, 2011, and other references described herein).

In one embodiment, the TRPVI channel activator is a capsaicinoid (e.g., capsaicin (8-methyl-N-vanillyl-trans-6-nonenamide)). Exemplary capsaicinoids are provided in Table 1.

TABLE 1

Exemplary capsaicinoids

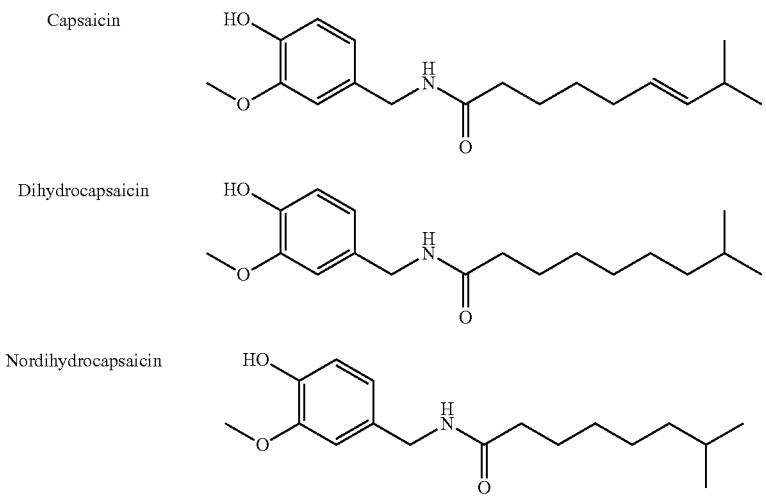

TABLE 1-continued

Exemplary capsaicinoids

Homodihydrocapsaicin

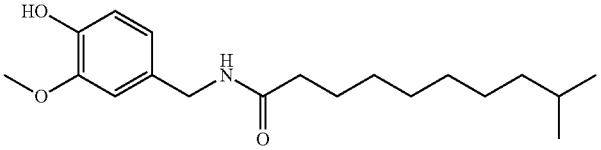 [SMILES: COc1cc(CNC(=O)CCCCCCCC(C)C)ccc1O]

Homocapsaicin

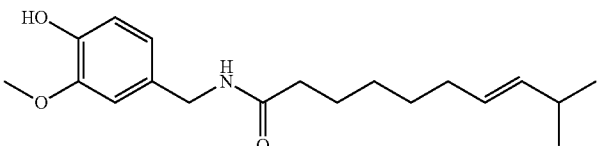

Nonivamide

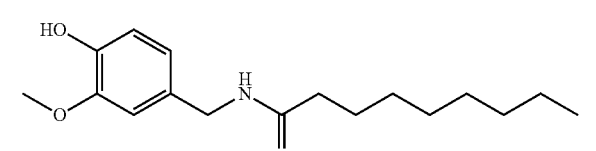

Suitable capsaicinoids and capsaicinoid analogs and derivatives for use in the compositions and methods of the present invention include naturally occurring and synthetic capsaicin derivatives and analogs including, e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl)methyl]-9Z-octa-decanamide, N-oleyl-homovanillamide, triprenylphenols (e.g., scutigeral), gingerols, piperines, shogaols, guaiacol, eugenol, zingerone, nuvanil, NE-19550, NE-21610, and NE-28345.

Other suitable TRPV1 channel activators include oleoylethanolamide, N-oleoyldopamine, 3-methyl-N-oleoyldopamine, oleamide, capsiate, 1-monoacylglycerols having C18 and C20 unsaturated and C8-C12 saturated fatty acid, 2-monoacylglycerols having C18 and C20 unsaturated fatty acids, miogadial, miogatrial, polygodial, and other terpenoids with an alpha,beta-unsaturated 1,4-dialdehyde moiety, sanshools, evodiamine, acesulfame-K, cyclamate, sulfates (e.g., $CuSO_4$, $ZnSO_4$, and $FeSO_4$), arvanil, anandamide, N-arachidonoyl-dopamine, flufenamic acid dopamide and other dopamine amides of fenamic acids, 4-hydroxynonenal, SA13353 (i.e., 1-[2-(1-adamantyl)ethyl]-1-pentyl-3-[3-(4-pyridyl)propyl]urea), gingerol or salts of magnesium.

In addition, the TRPV1 channel activator may be an analog or derivative of any of the TRPV1 channel activators described herein.

Additional TRPV1 channel activators are described, for example, in U.S. Pat. Nos. 7,632,519; 7,446,226; 7,429,673; 7,407,950; 6,022,718; 5,962,532; 5,762,963; 5,403,868; 5,290,816; 5,221,692; 4,812,446; 4,599,342; 4,564,633; 4,544,669; 4,544,668; 4,532,139; 4,493,848; 4,424,205; 4,313,958; in U.S. Patent Application Publication Nos. 2007/0293703; 2007/0167524; 2006/0240097; and 2005/0085652; and in WO 00/50387, each of which is incorporated by reference.

In addition, the TRPV1 channel activator may be an acidulant (e.g., acetic acid, phosphoric acid, citric acid, malic acid, succinic acid, tartaric acid, fumaric acid, or ascorbic acid) maintaining a low pH in the range of 2.5-6.5 (e.g., pH of 2.5, 3.0, 3.5, 4.0, 4.5, 5.0, 5.5, 6.0, or 6.5).

TRPV1 channel activators for use in the compositions and methods described herein can be identified using standard methodology, as described, for example, in U.S. Patent Application Publication No. 2003/0104085, which is hereby incorporated by reference. Exemplary assays for identification of TRPV1 channel activators include, without limitation, receptor binding assays; functional assessments of stimulation of calcium influx or membrane potential in cells expressing the TRPV1 receptor; assays for the ability to induce cell death in such cells (e.g., selective ablation of C-fiber neurons); and other assays known in the art.

A TRPV1 channel activator may be present in a composition of the invention at a concentration range of about 0.01% to 10% by weight by weight based on the total volume of the composition (e.g., 0.01, 0.1, 0.5, 1, 2, 3, 4, 5, 6, 7, 8, 9, or 10%), though a TRPV1 channel activator may be present in lower or higher concentrations.

TRPA1 Channel Activators

TRPA1 channels are activated by naturally occurring substances including, e.g., mustard oil, isothiocyanate compounds (e.g., allyl isothiocyanate), acrolein, farnesyl thiosalicylic acid, $\Delta_9$-tetrahydrocannabinol (THC), eugenol, ginger, gingerol, gingerols, shogaols, nicotine, nicotine derivatives and analogs, methyl salicylate, cinnamaldehyde, cinnamon oil, wintergreen oil, clove oil, allicin, diallyl sulfide, diallyl disulfide, diallyl trisulfide, sanshools, farnesyl thiosalicylic acid, and farnesyl thioacetic acid. The TRPA1 channel activator may also be an analog or derivative of any of the TRPA1 channel activators described herein, and additional TRPA1 channel activators are identified in WO 2009/071631, hereby incorporated by reference. Still other modulators of TRPA1 are described in, e.g., Harteneck et al., "Synthetic modulators of TRP channel activity," *Adv Exp Med Biol.* 704:87-106, 2011; Viana et al. "TRPA1 modulators in preclinical development," *Expert Opin. Ther. Pat.* 19 (12):1787-99, 2009).

Methods for identifying TRPA1 channel activators are known in the art and are described, for example, in U.S. Pat. No. 7,674,594.

A TRPA1 channel activator may be present in a composition of the invention at a concentration range of about 0.01% to 10% by weight by weight based on the total volume of the composition (e.g., 0.01, 0.1, 0.5, 1, 2, 3, 4, 5, 6, 7, 8, 9, or 10%), though a TRPA1 channel activator may be present in lower or higher concentrations.

ASIC Channel Activators

ASIC channels are activated by low pH. The pH of a composition of the present invention that includes an ASIC channel activator may be in the range of 2.5-6.5 (e.g., pH of 2.5, 3.0, 3.5, 4.0, 4.5, 5.0, 5.5, 6.0, or 6.5). The pH may be adjusted within this range by any means acceptable for compositions that are intended to be ingested by a subject. Exemplary acidulants are acetic acid, phosphoric acid, citric acid, malic acid, succinic acid, tartaric acid, fumaric acid, and ascorbic acid. The acidulant may be present in a composition of the invention at a concentration range of about 0.01% to 10% by weight based on the total volume of the composition (e.g., 0.01, 0.1, 0.5, 1, 2, 3, 4, 5, 6, 7, 8, 9, or 10%), though the acidulant may be present in lower or higher concentrations.

Additional Components of the Composition

The composition of the present invention may additionally include, for example, electrolytes (e.g., potassium salt or other salts), sweeteners, flavoring and coloring agents, vitamins, minerals, preservatives, and antioxidants.

Viscosity and Viscosity Modifiers

Viscosity is the ratio of shear stress to shear rate, expressed as dynes-second/cm$^2$, or poise. A centipoise (cP) is one one-hundredth of a poise.

The composition of the present invention may have a viscosity greater than water (i.e., about 1.0 cP at 20° C.), e.g., about 1.00, 200, 300, 400, 500, 1000, 1500, 2000, 2500, 3000, 3500, 4000, 4500, 5000, 6000, 7000, 8000, 9000 cP or more. if a consistency of corn syrup is desired, viscosities in the range of about 2500 cP are suitable. If a consistency of a soft gel or honey is desired, viscosities in the range of about 10000 cP to about 15000 cP are suitable. For pudding-like products, viscosities in the range of about 30000 cP to about 38000 cP are desirable. Viscosity of the compositions of the present invention may be measured with, e.g., a rheometer or viscometer, though additional methods of measuring viscosity are known in the art.

Viscosity modifiers may be added to compositions of the present invention. Such viscosity modifiers include, for example, collagen, gellan gum, carbohydrate gel-forming polymers, carob bean gum, locust bean gum, carrageenan, alginates (e.g., alginic acid, sodium alginate, potassium alginate, ammonium alginate, and calcium alginate), agar, guar gum, xanthan aura, carboxymethyl cellulose, clear starch, pectin, gelatin, arrowroot, cornstarch, katakuri starch, potato starch, sago, tapioca, furcellaran, and sodium pyrophosphate. A viscosity modifier my be present in the composition in an amount of from about 0.01% to 10% by weight based on the total volume of the composition (e.g., 0.01, 0.1, 0.5, 1, 2, 3, 4, 5, 6, 7, 8, 9, or 10%), though the viscosity modifier may be present in lower or higher concentrations.

Electrolytes

Exemplary electrolytes include potassium salts, chloride salts, bromide salts, sodium salts, magnesium salts, calcium salts, citrate salts, acetate salts, phosphate salts, salicylates, bicarbonate salts, lactate salts, sulphate salts, tartrate salts, benzoate salts, selenite salts, molybdate salts, iodide salts, oxides, and combinations thereof. An electrolyte may be present in a composition of the invention at a concentration range of about 0.01% to 10% by weight based on the total volume of the composition (e.g., 0.01, 0.02, 0.03, 0.04, 0.05, 0.1, 0.5, 1, 2, 3, 4, 5, 6, 7, 8, 9, or 10%), though an electrolyte may be present in lower or higher concentrations.

In certain embodiments, the compositions of the present invention include high concentrations of potassium (e.g., potassium chloride). The concentration of potassium in the composition may be, e.g., 0.01, 0.02, 0.03, 0.04, 0.05, 0.1, 0.5, 13, 4, 5, 6, or 7% or more by weight based on the total volume of the composition.

In certain embodiments, the compositions of the present invention include high concentrations of magnesium (e.g., magnesium chloride). The concentration of magnesium in the composition may be, e.g., 0.01, 0.02, 0.03, 0.04, 0.05, 0.1, 0.5, 1, 2, 3, 4, 5, 6, or 7% or more by weight based on the total volume of the composition.

Sweeteners

Sweeteners my be included in the compositions of the invention. Exemplary sweeteners include high fructose corn syrup, mannose, maltose, glucose polymers, sucrose (e.g., cane sugar or beet sugar), glucose, dextrose, lactose, galactose, fructose, polysaccharides (e.g., malodextrins), rice syrup, honey, and natural fruit juices (e.g., orange juice, papaya juice, pineapple juice, apple juice, grape juice, apricot juice, pear juice, tomato juice, agave nectar, or cranberry juice). Additionally, non- or low-caloric sweeteners can be used in the compositions of the invention. Examples of such non-caloric or low-caloric sweeteners include, but are not limited to, saccharin, cyclamates, acetosulfam, sorbitol, sucralose, xylitol, erythritol, Stevia extract, L-aspartyl-L-phenyl-alanine ester (e.g., aspartame), L-aspartyl-D-alanine alkyl amides, L-aspartyl-L-1-hydroxymethylalkaneamide, and L-aspartyl-1-hydroxyethylalkaneamide. Sweeteners may be present in a composition of the invention at a concentration range of about 2% to 20% by weight based on the total volume of the composition (e.g., 2, 3, 4, 5, 6, 7, 8, 9, 10, 11, 12, 13, 14, 15, 16, 17, 18, 19, or 20%), though sweeteners may be present in lower or higher concentrations.

Flavoring and Coloring Agents

Exemplary flavoring agents include almond oil, amaretto oil, anethole, anise oil, benzaldehyde, blackberry, black walnut oil, blueberry, caraway, caraway oil, cardamom oil, cardamom seed, cherry juice, cherry syrup, cinnamon, cinnamon oil, cinnamon water, citric acid, citric acid syrup, clove oil, cocoa, coriander oil, dextrose, eriodictyon, ethyl acetate, ethyl vanillin, fennel oil, ginger, glucose, glycerin, glycyrrhiza, grape, honey, lavender oil, lemon oil, lime, mannitol, methyl salicylate, myristica oil, orange oil, orange peel, orange syrup, peppermint, peppermint oil, peppermint water, phenylethyl alcohol, pineapple, raspberry juice, raspberry syrup, rosemary oil, rose oil, rose water, sarsaparilla syrup, sorbitol, spearmint, spearmint oil, strawberry, sucrose, thyme oil, tolu balsam, vanilla, vanillin, and wild cherry syrup. Additional flavoring agents may be found in Food Chemicals Codex and Fenaroli's Handbook of Flavor Ingredients.

Small amounts of one or more coloring agents may be utilized in the compositions of the present invention. Coloring agents include, e.g., beta-carotene, riboflavin dyes, FD&C dyes (e.g., Yellow No. 5, Blue No. 1, Blue No. 2, and Red No. 40), FD&C lakes, chlorophylls and chlorophyllins, caramel coloring, annatto, cochineal, turmeric, saffron, paprika, and fruit, vegetable, and/or plant extracts (e.g., grape, black currant, aronia, carrot, beetroot, red cabbage, elderberry, and hibiscus extracts). The amount of coloring agent used will vary depending on the agents used in the composition and the color intensity desired in the finished product. The amount of coloring agent to be used can be readily determined by one skilled in the art.

Vitamins and Minerals

Non-limiting examples of vitamins and minerals that may be included in the compositions of the present invention include, e.g., choline bitartate, niacinamide, thiamin, folic acid, d-calcium pantothenate, biotin, vitamin A, vitamin C, vitamin $B_1$ hydrochloride, vitamin $B_2$, vitamin $B_3$, vitamin $B_6$ hydrochloride, vitamin $B_{12}$, vitamin D, vitamin E acetate, vitamin K, and salts of calcium, potassium, magnesium, zinc, iodine, iron, and copper. When included in a composition of the invention, the composition contains at least 5, 10, 15, 20, 25, 30, 35, 40, 45, or 50% of the U.S. recommended daily intake (RDI) for such vitamins and minerals.

Preservatives

One or more preservatives may additionally be utilized in the compositions described herein. Exemplary preservatives include, for example, sorbate, benzoate, and polyphosphate preservatives (e.g., sorbic acid, benzoic acid, calcium sorbate, sodium sorbate, potassium sorbate, calcium benzoate, sodium benzoate, potassium benzoate, and mixtures thereof). When included in a composition of the invention, the preservative is included at levels from about 0.0005% to about 0.5% (e.g., 0.0005, 0.001, 0.005, 0.01, 0.05, 0.1, or 0.5%) by weight based on the total volume of the composition, though preservatives may be present in lower or higher concentrations.

Antioxidants

One or more antioxidant agents may also be included in the compositions to, for example, reduce exercise-induced oxidative stress. Exemplary antioxidants include vitamin C and vitamin E; beta-carotene, lutein, or other carotenoids; cyanidin, delphinidin, malvidin, or other anthocyanidins; apigenin, luteolin, or other flavones; hesperitin, naringenin, or other flavonones; isorhamnetin, quercetin, kaempferol or other flavonols; and epigallocatechin-3-gallate, epicatechin, thearubigins, or other flavan-3-ols.

Additional components of the compositions described herein may include amino acids (e.g., leucine, isoleucine, lysine, methionine, phenylalanine, threonine, tryptophan, and valine), stimulants (e.g., caffeine), emulsifying agents, carbon dioxide (e.g., to carbonate a liquid composition), stabilizers, humectants, anticaking agents, or herbal extracts.

Combination Therapies

In certain embodiments, additional therapeutic agent(s) may be administered with compositions of the present invention for, e.g., the treatment or amelioration of muscle cramps and/or the recovery of muscles from exercise fatigue. Such therapeutic agents include, for example, muscle relaxants (e.g., diazepam) or anti-inflammatory agents (e.g., ibuprofen). When combination therapy is employed, the additional therapeutic agent(s) can be administered as a separate formulation or may be combined with any of the compositions described herein.

For example, any of the compositions described herein can be used for the treatment of nocturnal (or night) cramps. In some embodiments, the compositions can be used in combination with one or more sleep aids. Sleep aids that can be used in combination with the compositions and methods described herein include: antihistamines (e.g., diphenhydramine and doxylamine); benzodiazepines estazolam (ProSom), flurazepam (Dalmane), quazepam (Doral), temazepam (Restoril), and triazolam (Halcion)); non-benzodiazepine sedative hypnotics (e.g., eszopiclone (Lunesta), zalepon (Sonata), and zolpidem (Ambien)); and melatonin receptor agonist hypnotics (e.g., ramelteon (Rozerem). Still other sleep aids that can be used in combination with the compositions and methods described herein include: chamomile, valerian root, kava kava, lemon balm, passionflower, lavender, St. John's Wort, melatonin, tryptophan (e.g., L-tryptophan), 5-hydroxytryptophan (5-HTP), catnip, hops, rhodiola, oatstraw, lavender, GABA, L-theanine, linden, ginseng (e.g., Siberian ginseng), honey, nutmeg, mugwort, butterbur, rauwolfia, taumelloolch, American hellebore, quassia, tulip tree, brewer's yeast, inositol, skullcap, phosphatidylserine, calcium, magnesium, vitamin B6, vitamin B12, and pantothenic acid (B5).

Formulations and Methods of Preparing Compositions

The compositions and solutions of the present invention may be formulated as ready-to-drink beverages, concentrates (e.g., syrups), dry compositions (e.g., powders, granules, or tablets that may be reconstituted with a liquid (e.g., with water), gels, solids, semi-solids (e.g., ice cream, pudding, or yogurt), frozen liquids (e.g., ice pops), lozenges or hard candies, dissolving strips (e.g., an edible strip containing pullulan and compositions of the invention), and chewing gum.

In some embodiments, the compositions may be in the form of a dry powder, granule, or tablet that may be reconstituted in a specified amount of a liquid. The dried components may be mixed together and milled (e.g., to create a homogenous powder) or mixed in aqueous solution and dried by using methods known to one of skill in the art. Dried powders or granules may be "loose" or fashioned into tablets.

The compositions described herein can be ingested, for example, by a subject before, during, or after exercise. The compositions and solutions described herein can be ingested (e.g., through eating or drinking) before the onset of muscle cramping, when muscle cramping begins, any time after the onset of muscle cramping, or after muscle cramping has subsided. The compositions of the solution can also be ingested after exercise to accelerate nerve-muscle recovery from exercise fatigue. When the compositions and solutions of the present invention are in the form of a ready-to-drink beverage, e.g., 1, 2, 4, 8, 10, 12, 14, 16, 18, 20, 24, 26, 28, 30, or 32 ounces of the beverage may be consumed as needed (e.g., once, twice, three, four, five, six times per day; once per week; or once per month).

The compositions and solutions of the present invention may be prepared using methods known to one of skill in the art. Such methods include dissolving, dispersing, or otherwise mixing all components singularly or in suitable combinations and agitating with, for example, a mechanical stirrer until all of the ingredients have been solubilized or adequately dispersed. Where a shelf-stable composition or solution is desired, the final mixture can be pasteurized, ultra-pasteurized, sterilized, or filled aseptically at appropriate process conditions. Where required for mutual stability of two or more components (for example if a component is unstable at low pH), multiple components can be mixed shortly before ingestion.

The compositions and solutions described herein may be bottled or packaged in, for example, glass bottles, plastic bottles and containers (e.g., polyethylene terephthalate or foil-lined ethylene vinyl alcohol), metal cans (e.g., coated aluminum or steel), lined cardboard containers, pouches, packs, wrappers, or any other packaging known to one of skill in the art. For example, a ready-to-drink beverage can be bottled or packaged in a unit that contains between 10-1000 mL of the beverage. For example, the packaging can contain 10, 20, 50, 100, 200, 300, 400, 500, 600, 700, 800, 900, or 1000 mL of the beverage. Alternatively, the packaging can contain 200, 250, 330, 350, 355, 375, 440, or 500 mL of the beverage. A ready-to-drink beverage can also be bottled or packaged in a unit that contains between 1-32 fluid ounces of beverage (e.g., the unit may contain 1, 2, 5, 6.75, 8, 8.3, 8.4, 8.45, 9.6, 10, 12, 15, 15.5, 16, 18.6, 20, 23, 24, or 32 fluid ounces). Where a shelf-stable composition or solution is desired, the packaging is appropriately sterilized before being filled by the pasteurized, ultra-pasteurized, or sterilized composition or solution. Where required for mutual stability of two or more components (for example if a component is unstable at low pH), the packaging may feature multiple containers that can be mixed shortly before ingestion or that can be consumed serially.

EXAMPLES

General Procedures
TRP-Stim Solution

The solution ("TRP-Stim") administered to the volunteers contained: a base of a 1:1 mixture of water and light karo syrup (for increased viscosity); 0.075% of a capsicum preparation intended for human use (Clearcap Super Soluble Caspsicum, Kalsec Inc.); 1% of a cinnamon volatile oil intended for human consumption (Aquaresin Cinnamon, Kalsec Inc); and 1.5% of a ginger oleoresin intended for human use (Aquaeresin Ginger, Kalsec Inc).

Electromyography (EMG) Measurements of Cramps

Methods for placing stimulating electrodes on the flexor hallucis brevis (FHB) or gastrocnemius muscles followed the procedures described by Minetto et al., *Muscle Nerve*, 40: 535-544, 2009. The active stimulation electrode (cathode) was a 1.25" circular mesh-backed silver patch electrode (Reliamed) and was placed so as to produce contraction of the FHB with minimal stimulation amplitude. The stimulation reference electrode was a 2" square patch electrode (Reliamed) placed on the opposite side of the foot. Cramping of the FHB was induced as described by Minetto et al. (ibid.) using a battery-powered electrical muscle stimulator (EMS-7500, Current Solutions LLC) to deliver pulses. A series of 180 microsecond biphasic square pulses of voltages were applied at various frequencies to stimulate the muscle. First, using slow (2 Hz) stimulation, the amplitude was adjusted to ~30% more than the threshold amplitude for eliciting strong contraction of the muscle. The muscle was then stimulated by a train of 180 microsecond pulses of this amplitude delivered for 5 seconds at various frequencies. The stimulation delivered by the stimulator also including "ramp up" and "ramp down" periods of 1 second preceding and following the main 5-sec stimulation period during which the amplitude of the pulses was ramped up or down to and from the final value.

It has been previously shown that susceptibility to cramping of the FHB using similar electrical stimulation protocols is highly reproducible within each subject (Minetto et al., *Muscle Nerve*, 37:90-100, 2008) and is correlated with susceptibility to "ordinary muscle cramps" (Miller et al., *Muscle Nerve*, 39:364-368, 2009).

Cramping was quantified by making EMG recordings from the belly of the FHB. Two external EMG recording electrodes (Vermed SilveRest) were placed along the belly of the FHB. The differential voltage relative to a third ground electrode placed at the ankle was amplified, digitized, and saved to computer using I-330-C:2+ EMG unit with PhysioLab software (J&J Engineering, Poulsbo, Wash.). The raw wide-band EMG signal (10-400 Hz) was processed by being rectified and integrated to provide the area under the curve (RMS). The duration of cramp was quantified by the time required for the RMS EMG to return to an amplitude of 3 standard deviations above the baseline value. This correlated well with duration of the cramp as observed by the return to the toe to resting position.

Recordings of cramps in calf muscles (medial gastrocnemius) were made using similar procedures, with placement of stimulation and recording electrodes following that by Minetto et al., *Muscle Nerve*, 40:535-544, 2009. The amplitude of stimulation by a single 180 microsecond biphasic square pulses was adjusted to be ~30% of the amplitude required for maximal contraction of the muscle. After a short period of slow stimulation (2 Hz), the frequency of stimulation was ramped up to 22-24 Hz over ~5 seconds and held at this frequency for an additional 5 seconds before terminating the stimulation. This protocol reliably induced cramping of 30-90 seconds.

Assay of Activation of Rat Sensory Neurons

Methods to monitor activation of primary sensory neurons isolated from the trigeminal ganglion of rats followed those published by Park et al., *Journal of Biological Chemistry*, 281:17304-17311, 2006). Cells isolated from rat trigeminal ganglia were loaded with the fluorescent calcium indicator Fura-2AM (Fura-2-acetoxymethyl ester), and increases in intracellular calcium reflecting activation of the neurons were measured as an increase in Fura-2 fluorescence as measured by digital video micro-fluorometry with an intensified CCD camera. The same capsicum extract, cinnamon extract, and ginger extract used in the TRP-Stim beverage were applied to the neurons after being diluted in balanced salt solution (in mM: 145 NaCl, 5 KCl, 2 $CaCl_2$, 1 $MgCl_2$, 10 HEPES, and 10 glucose) which perfused the neurons. Caspicum extract was applied at a dilution of 1/800,000, cinnamon extract at a dilution of 1/5,000, and ginger extract at a dilution of 1/12,000. In some experiments the calcium ionophore ionomycin was added following the tests with extracts to produce a large entry of calcium as an index of the maximal possible signal, illustrating the strength of activation by the heavily diluted extracts.

Example 1

Activation of Rat Sensory Neurons by Capsicum, Cinnamon, and Ginger Extracts

FIG. 1 shows graphs from six sensory neurons isolated from the trigeminal ganglia of rats, illustrating their activation by the capsicum, cinnamon, and ginger extracts that were used in the human experiments. Activation was quantified as an increase in intracellular free calcium, monitored by a fluorescent calcium indicator. Extracts were diluted into normal extracellular saline (Tryrode's solution) and were tested at lower concentrations than used in the beverage, taking account that concentrations present at nerve endings in mouth, esophagus, or stomach are expected to be lower than the beverage as a result of dilution into mucosa and interstitial fluid. All three extracts were capable of activating individual neurons when applied at concentrations 50-fold to 15,000-fold lower than used in the beverage. Each trace shows a record from a different neuron, illustrating that some neurons could be activated by each of the extracts and that the strength of activation by each extract varied among particular neurons. These records illustrate that each agent is capable of acting alone to activate sonic neurons and that a combination of agents can produce stronger activation of a larger fraction of neurons. Further, the bottom two records show that there can be strongly synergistic activation of neurons by the capsicum extract and the ginger extract when applied in combination.

Example 2

Effect of TRP-Stim Administration to Human Subjects

The in vitro data of Example 1 show that each individual component of the TRP-Stim solution by itself was capable of activating sensory neurons. Consistent with this, human experiments showed the efficacy of a beverage with capsicum alone (ClearCap capsicum at 1/2000 dilution) to inhibit cramping, achieved within 5 minutes.

The in vitro data also show that combinations of channel activators can not only show the desired activity, but can also provide synergistic effects. The following experiments, illustrated by FIGS. 2-8, show cramp relief by the administration of a uniform beverage composition designed for maximal TRP stimulation containing capsicum, cinnamon extract, and ginger extract, and where the physiological effects were monitored by EMG recording.

Figure 6:
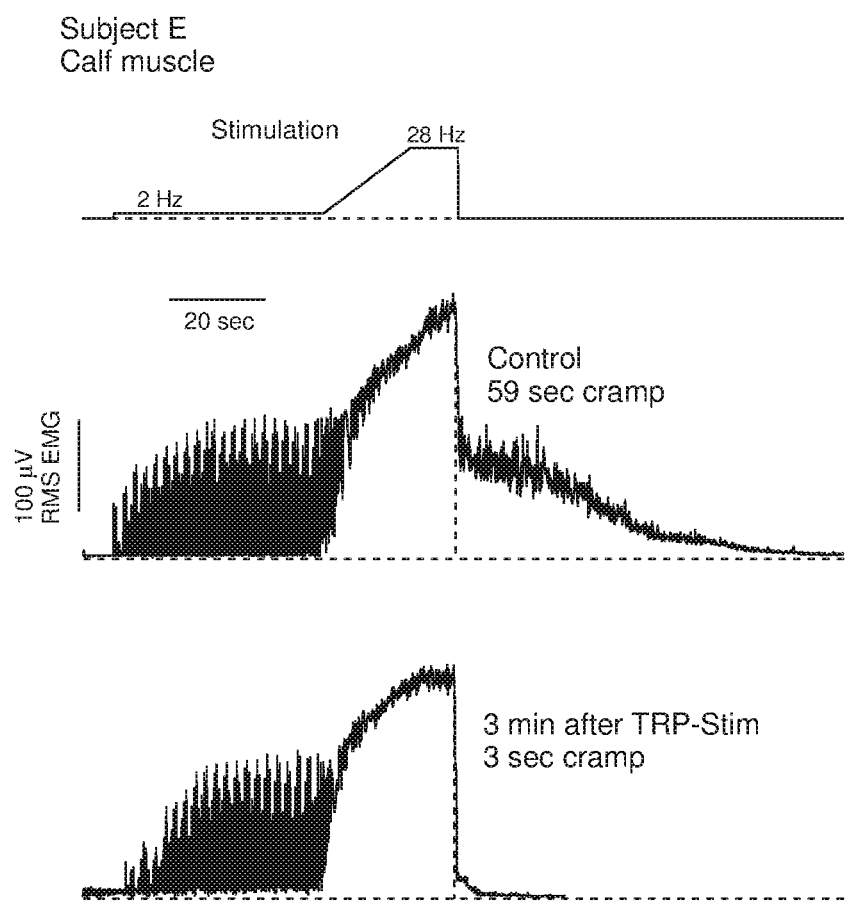
FIG. 6 is a graph showing the effect of the TRP-Stim beverage on cramping of the gastrocnemius (calf) muscle of a fifth subject. The muscle was stimulated, and after cessation of stimulation, the muscle went into a prolonged cramp lasting 59 seconds. In test 3 minutes after ingestion of 50 mL of TRP-Stim, cramping was abolished.
Figure 7:
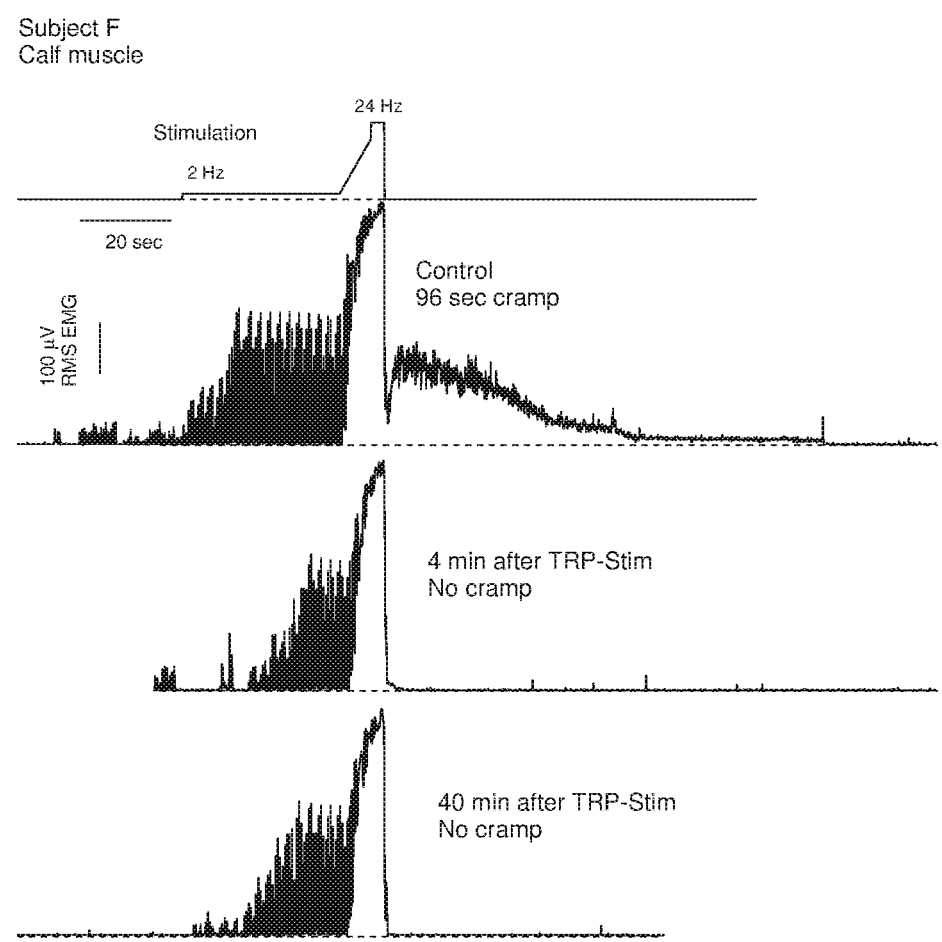
FIG. 7 shows the effect of the TRP-Stim beverage on cramping of the gastrocnemius (calf) muscle of a sixth subject. The muscle was stimulated, and after cessation of stimulation, the muscle went into a prolonged cramp lasting 96 seconds. In a test 4 minutes after ingestion of 50 mL of TRP-Stim, cramping was abolished. Cramping was still abolished in a test conducted 40 minutes later.
Figure 8:
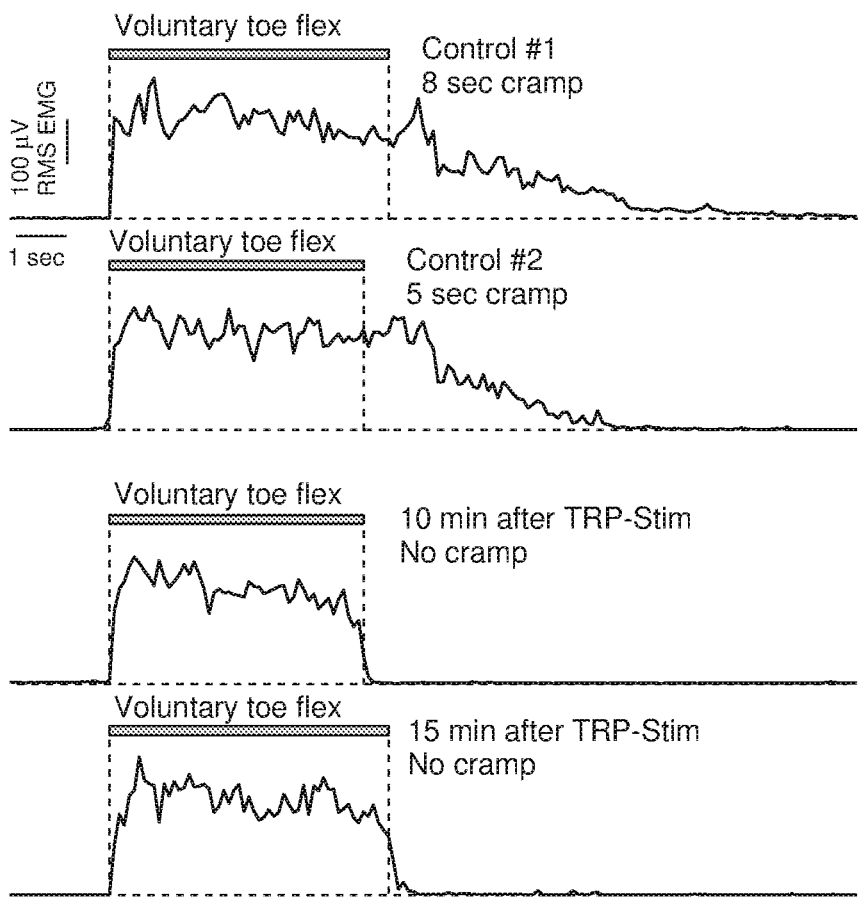
FIG. 8 is a graph showing the effect of the TRP-Stim beverage on cramping of an FHB muscle in a seventh subject who experienced spontaneous cramping induced by pointing her toe. Ten minutes after the subject ingested 50 mL of the TRP-Stim beverage, cramping was abolished.

FIGS. 2-8 are graphs of EMG recordings of muscle contractions in seven human volunteers (four females and three males) that show the efficacy in preventing and treating cramps of ingesting 50 mL of a solution designed to stimulate TRPV1 and TRPA1 receptors in the mouth, esophagus, and stomach. Muscle cramps were induced by brief stimulation of toe or calf muscles (FIGS. 2-7) or occurred spontaneously (FIG. 8). After recording cramping in control, subjects drank 50 mL of the TRP-Stim solution containing capsaicin and capsaicinoids (TRPV1 agonists), cinnamaldehyde (TRPA1 agonist), and gingerols (TRPA1 and TRPV1 agonists). After ingestion of the solution, subjects were tested for muscle cramping using the same procedures as in control at times ranging from 4 minutes to 11 hours after ingestion.

Eight human volunteers were tested using the TRP-Stim beverage. Seven of the eight showed a complete abolition or dramatic reduction in cramping following ingestion of the beverage (FIGS. 2-8). The effect was typically complete within 4-15 minutes and lasted for 2½ to 4 hours in different subjects. An eighth subject showed cramping of the FHB that was not dramatically affected by the TRP-Stim beverage. The cramping in this subject was of much lower EMG amplitude that the other subjects and appeared to involve repetitive contraction of only a few motor units.

FIG. 2 is a graph showing the effect of the TRP-Stim beverage on cramping of the flexor hallucis brevis of Subject A. Under control conditions, cramping was reliably induced by stimulating the muscle using an electrical muscle stimulator (EMS-7500, Current Solutions LLC) placed with external electrodes for FHB stimulation. Muscle activity was recorded using external electrodes placed over the belly of the muscle attached to an EMG amplifier (J&J Engineering I-330C2+). In control, stimulation using 180 microsecond biphasic pulses delivered at 18 Hz for 5 seconds reliably and reproducibly produced cramping of the muscle, which was evident by EMG activity continuing after the cessation of stimulation. After ingestion of the TRP-Stim beverage, cramping was very brief after 11 minutes and essentially absent at tests at 20 minutes and 2½ hours after ingestion.

Figure 3:
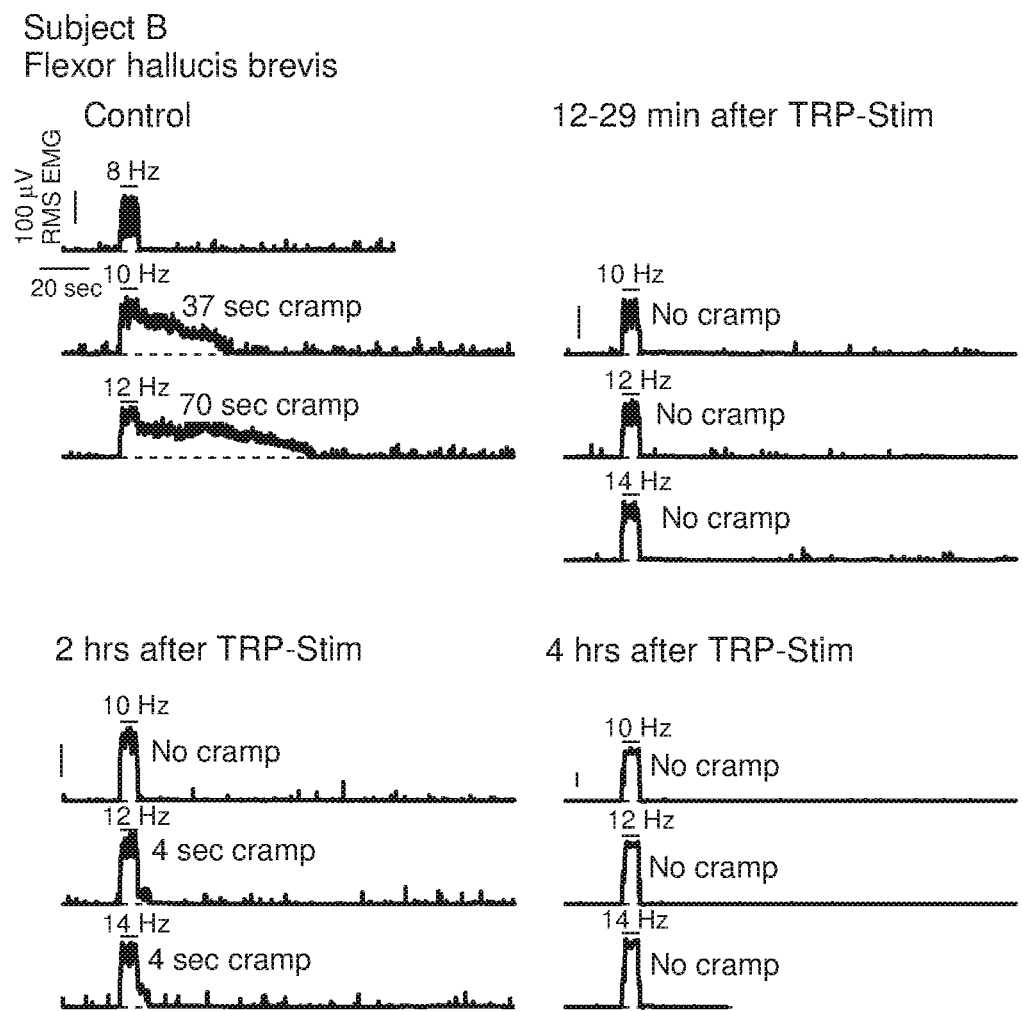
FIG. 3 shows the effect of the TRP-Stim beverage on cramping of the FHB of a second subject after cramping was induced. In recordings beginning 12 minutes after ingestion of the TRP-Stim beverage, stimulation at 10 Hz or 12 Hz produced essentially no cramping, and increasing the frequency of stimulation to 14 Hz also did not induce cramping. The dramatic reduction in cramping was still present 4 hours later in this subject.

FIG. 3 is a graph showing the effect of the TRP-Stim beverage on cramping of the flexor hallucis brevis of a second subject. Under control conditions, cramping was induced by stimulation at 10 Hz for 5 seconds (1.80 microsecond pulses, amplitude set to ~30% higher than threshold for muscle contraction), and a longer cramp was induced by increasing the frequency to 12 Hz. In recordings beginning 12 minutes after ingestion of the TRP-Stim beverage, stimulation at 10 Hz or 12 Hz produced essentially no cramping, and increasing the frequency of stimulation to 14 Hz also did not induce cramping. The dramatic reduction in cramping was still present 4 hours later in this subject.

Figure 4:
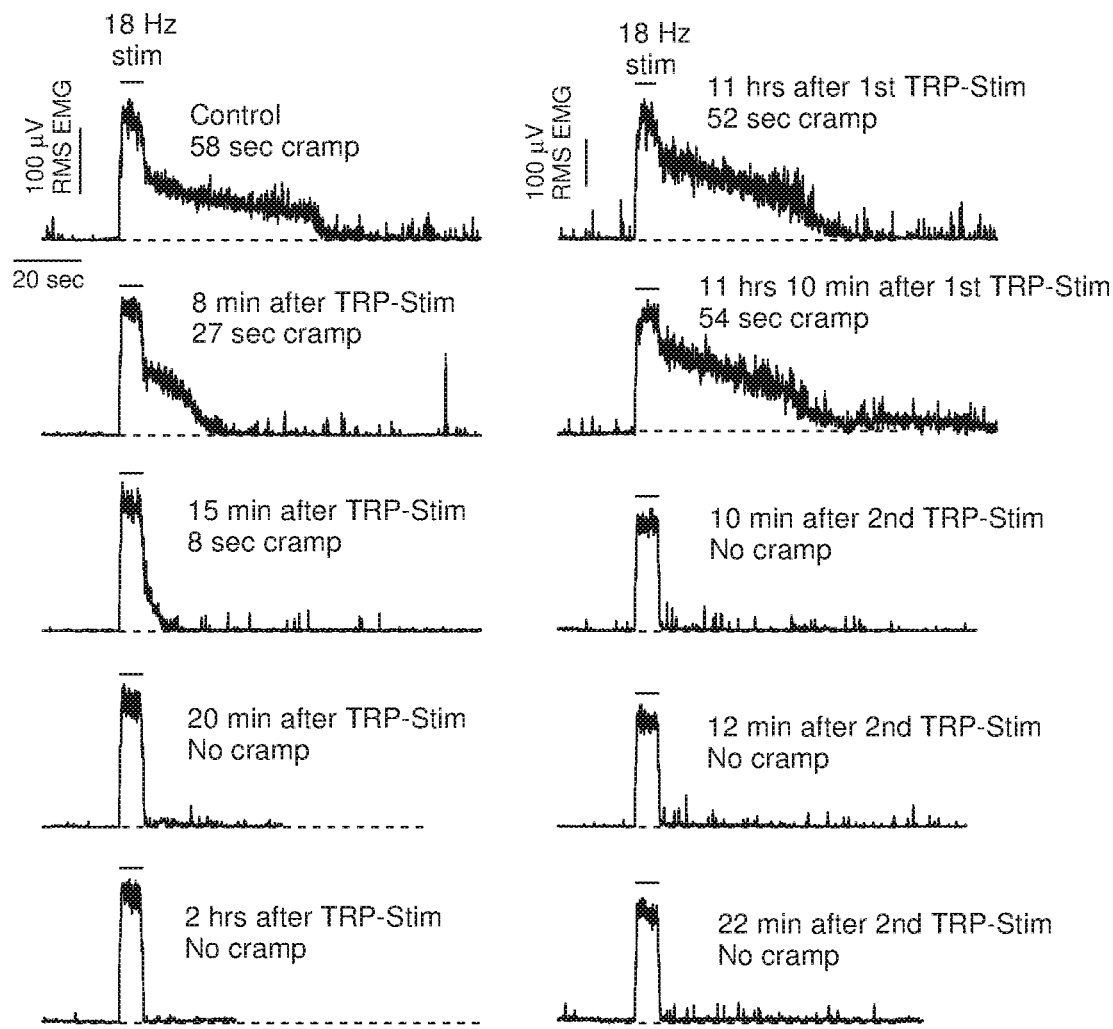
FIG. 4 shows the effect of the TRP-Stim beverage on cramping of the FHB of a third subject tested over longer times. Under control conditions, a cramp lasting 58 seconds was induced. After ingestion of the TRP-Stim beverage, the duration of the cramp was reduced to 27 seconds after 8 minutes, to 8 seconds after 15 minutes, and cramping was abolished after 20 minutes and in a test after 2 hours. In tests 11 hours after ingestion, reliable cramping had returned. After the subject again drank 50 mL of the TRP-Stim beverage, cramping was completely abolished in tests beginning after 10 minutes.

FIG. 4 is a graph showing the effect of the TRP-Stim beverage on cramping of the flexor hallucis brevis of a third subject tested over longer times. Under control conditions, a cramp lasting 58 seconds was induced by stimulation at 18 Hz for 5 seconds (180 microsecond pulses, amplitude set to ~30% higher than threshold for muscle contraction). After ingestion of the TRP-Stim beverage, the duration of the cramp was reduced to 27 seconds after 8 minutes and to 8 seconds after 15 minutes. Cramping was abolished after 20 minutes and in a test after 2 hours. In tests 11 hours after ingestion, reliable cramping had returned. After the subject again drank 50 mL of the TRP-Stim beverage, cramping was completely abolished in tests beginning after 10 minutes.

Figure 5:
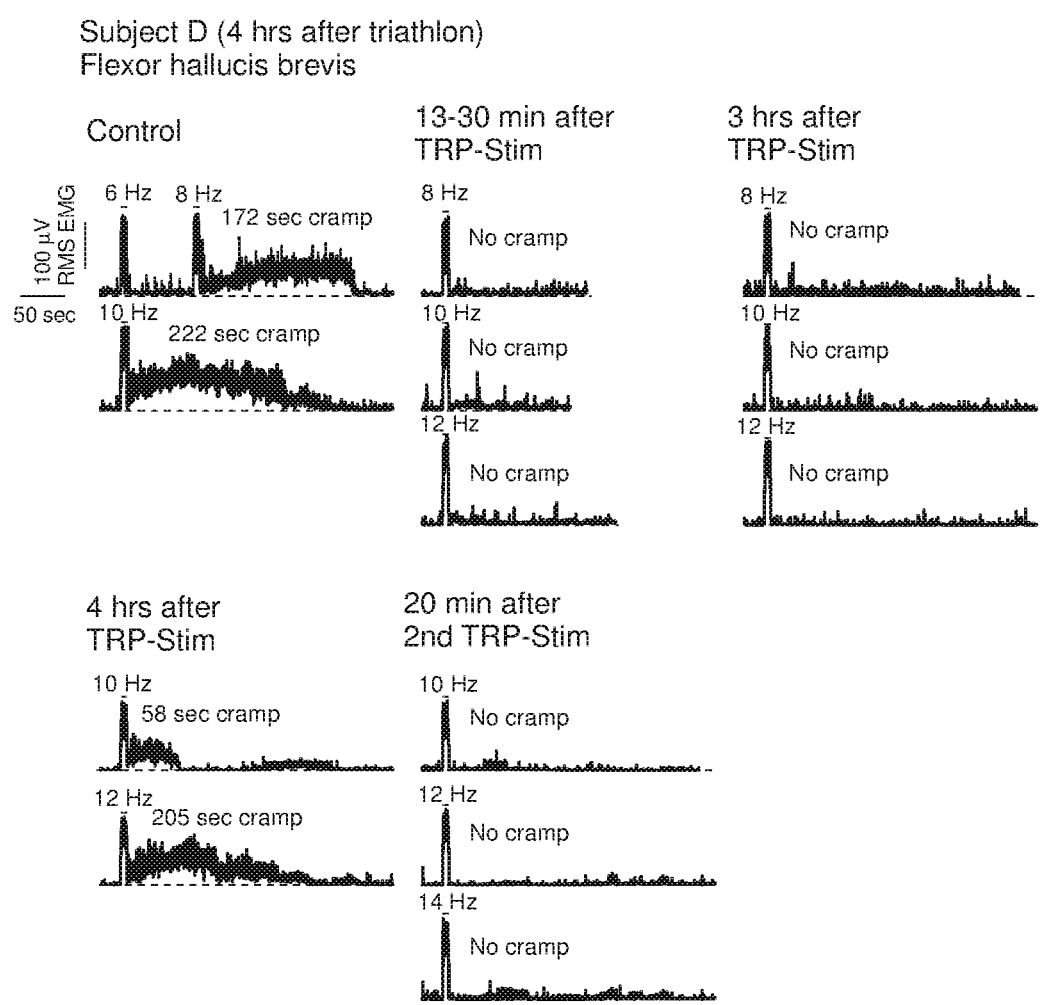
FIG. 5 shows the effect of the TRP-Stim beverage on cramping of the FHB of a fourth subject. This subject had engaged in strenuous exercise (triathlon) four hours earlier and was experiencing muscle twitchiness. This subject had an unusually low frequency threshold (8 Hz) for induction of cramping in the FHB muscle, and the resulting cramps were unusually long (172 seconds after 8 Hz stimulation and 222 seconds after 10 Hz stimulation). Cramping was completely gone in tests starting 13 minutes after ingestion of the TRP-Stim beverage, even when increasing the stimulation frequency to 12 Hz. Cramping was still abolished 3 hours later. After 4 hours, cramping returned, but with an increased frequency threshold (10 Hz). After the subject again drank 50 mL of the TRP-Stim beverage, cramping was again completely abolished.

FIG. 5 is a graph showing the effect of the TRP-Stim beverage on cramping of the flexor hallucis brevis of a fourth subject. This subject had engaged in strenuous exercise (triathlon) four hours earlier and was experiencing muscle twitchiness. This subject had an unusually low frequency threshold (8 Hz) for induction of cramping in the FHB muscle, and the resulting cramps were unusually long (172 seconds after 8 Hz stimulation and 222 seconds after 10 Hz stimulation). Cramping was completely gone in tests starting 13 minutes after ingestion of the TRP-Stim beverage, even when increasing the stimulation frequency to 12 Hz. Cramping was still abolished 3 hours later. After 4 hours, cramping returned with an increased frequency threshold (10 Hz) and shorter cramps than in control. After the subject again drank 50 mL of the TRP-Stim beverage, cramping was again completely abolished.

FIG. 6 is a graph showing the effect of the TRP-Stim beverage on cramping of the gastrocnemius (calf) muscle of a fifth subject. The muscle was stimulated by a protocol ramping the frequency of stimulation from 2 Hz to 28 Hz (180 microsecond pulses, amplitude set to ~30% higher than threshold for muscle contraction). After cessation of stimulation, the muscle went into a prolonged cramp lasting 59 seconds. In a test 3 minutes after ingestion of 50 mL of TRP-Stim, cramping was abolished.

FIG. 7 is a graph showing the effect of the TRP-Stim beverage on cramping of the gastrocnemius (calf) muscle of a sixth subject. The muscle was stimulated by a protocol ramping the frequency of stimulation from 2 Hz to 24 Hz (180 microsecond pulses, amplitude set to ~30% higher than threshold for muscle contraction). After cessation of stimulation, the muscle went into a prolonged cramp lasting 96 seconds. In a test 4 minutes after ingestion of 50 mL of TRP-Stim, cramping was abolished. Cramping was still abolished in a test conducted 40 minutes later.

FIG. 8 is a graph showing the effect of the TRP-Stim beverage on cramping of an FHB muscle in a seventh subject, who experienced spontaneous cramping induced by pointing her toe. In control conditions, voluntary toe flexes lasting ~5 seconds reliably produced cramping of the FHB lasting 5-8 seconds in different trials. Ten minutes after the subject ingested 50 mL of the TRP-Stim beverage, cramping was abolished.

OTHER EMBODIMENTS

From the foregoing description, it is apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

What is claimed is:

1. A method of treating muscle cramping in a subject in need thereof, the method comprising orally administering to the subject a liquid composition comprising capsaicinoid, cinnamaldehyde, a gingerol, and an excipient, wherein the liquid composition comprises 0.001% to 1% weight/weight (w/w) capsaicinoids per weight of the liquid composition or 0.0001-0.01 mgs of total capsaicinoids/mL of the liquid composition and a total of 0.001% to 1% weight/weight (w/w) of a gingerol per weight of the liquid composition.

2. The method of claim 1, wherein the muscle cramping results from exercise, nocturnal cramps, or menstrual cramps.

3. The method of claim 1, wherein the muscle cramping results from nocturnal cramps.

4. The method of claim 1, wherein the liquid composition is administered prior to, during, or after the muscle cramping.

5. The method of claim 1, wherein the liquid composition comprises a beverage or a spray.

6. The method of claim 1, wherein the capsaicinoid comprises capsaicin.

7. The method of claim 1, wherein the liquid composition further comprises an electrolyte.

8. The method of claim 1, wherein the excipient comprises a disintegrant, a binder, a surfactant, an emulsifier, a viscosity modifier, a lubricant, a sweetener, a pH-adjusting agent, a preservative, a flavoring agent, a coloring agent, or an antioxidant.

9. The method of claim 8, wherein the excipient is selected from gellan gum, carob bean gum, locust bean gum, carrageenan, alginates, agar, guar gum, xanthan gum, carboxymethyl cellulose, clear starch, pectin, gelatin, cornstarch, katakuri starch, potato starch, and gum arabic.

10. The method of claim 8, wherein the excipient comprises a sweetener selected from high fructose corn syrup, mannose, maltose, glucose polymers, sucrose, glucose, dextrose, lactose, galactose, fructose, polysaccharides, rice syrup, honey, saccharin, cyclamates, acetosulfam, sorbitol, sucralose, xylitol, erythritol, Stevia extract, L-aspartyl-L-phenyl-alanine ester, L-aspartyl-D-alanine alkyl amides, L-aspartyl-L-1-hydroxymethylalkaneamide, and L-aspartyl-1-hydroxyethylalkaneamide.

11. The method of claim 8, wherein the excipient comprises a pH-adjusting agent selected from hydrochloric acid, citric acid, sodium hydrogen carbonate, potassium hydroxide, sodium hydroxide, and sodium carbonate.

12. The method of claim 8, wherein the excipient comprises a preservative selected from sorbic acid, benzoic acid, sodium benzoate, calcium benzoate, potassium benzoate, potassium sorbate, calcium sorbate, and sodium sorbate.

13. The method of claim 8, wherein the excipient comprises a flavoring agent selected from almond oil, amaretto oil, anethole, anise oil, benzaldehyde, blackberry, black walnut oil, blueberry, caraway, caraway oil, cardamom oil, cardamom seed, cherry juice, cherry syrup, cinnamon, cinnamon oil, cinnamon water, citric acid, citric acid syrup, clove oil, cocoa, coriander oil, dextrose, eriodictyon, ethyl acetate, ethyl vanillin, fennel oil, ginger, glucose, glycerin, glycyrrhiza, grape, honey, lavender oil, lemon oil, lime, mannitol, methyl salicylate, myristica oil, orange oil, orange peel, orange syrup, peppermint, peppermint oil, peppermint water, phenylethyl alcohol, pineapple, raspberry juice, raspberry syrup, rosemary oil, rose oil, rose water, sarsaparilla syrup, sorbitol, spearmint, spearmint oil, strawberry, sucrose, thyme oil, tolu balsam, vanilla, vanillin, and wild cherry syrup.

\* \* \* \* \*